US009637718B2

(12) United States Patent
Vanapalli et al.

(10) Patent No.: US 9,637,718 B2
(45) Date of Patent: May 2, 2017

(54) METHODS AND DEVICES TO CONTROL FLUID VOLUMES, REAGENT AND PARTICLE CONCENTRATION IN ARRAYS OF MICROFLUIDIC DROPS

(75) Inventors: Siva A. Vanapalli, Lubbock, TX (US); Swastika S. Bithi, Lubbock, TX (US); Meng Sun, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 14/114,304

(22) PCT Filed: May 7, 2012

(86) PCT No.: PCT/US2012/036815
§ 371 (c)(1),
(2), (4) Date: Oct. 28, 2013

(87) PCT Pub. No.: WO2012/154688
PCT Pub. Date: Nov. 15, 2012

(65) Prior Publication Data
US 2014/0051062 A1    Feb. 20, 2014

Related U.S. Application Data

(60) Provisional application No. 61/483,087, filed on May 6, 2011, provisional application No. 61/604,785, filed on Feb. 29, 2012.

(51) Int. Cl.
*C12M 1/00*      (2006.01)
*B01L 3/00*      (2006.01)
*G01N 35/10*    (2006.01)

(52) U.S. Cl.
CPC ....... *C12M 47/02* (2013.01); *B01L 3/502784* (2013.01); *G01N 35/1002* (2013.01); *B01L 2200/0668* (2013.01); *B01L 2200/0673* (2013.01); *B01L 2300/088* (2013.01); *B01L 2400/0487* (2013.01); *G01N 2035/1034* (2013.01); *Y10T 29/49* (2015.01)

(58) Field of Classification Search
CPC .................................................... C12M 47/02
See application file for complete search history.

(56) References Cited

U.S. PATENT DOCUMENTS

2003/0138359 A1   7/2003   Chow et al.
2009/0266421 A1   10/2009  Linder et al.
(Continued)

FOREIGN PATENT DOCUMENTS

WO    2009139898 A2   11/2009

OTHER PUBLICATIONS

Korczyk, P. M. et al., "Effects of unsteadiness of the rates of flow on the dynamics of formation of droplets in microfluidic systems", Lab Chip, 2011, 11, 173-175.
(Continued)

*Primary Examiner* — Brian R Gordon
(74) *Attorney, Agent, or Firm* — Daniel J. Chalker; Edwin S. Flores; Chalker Flores, LLP

(57) ABSTRACT

The present invention includes a microfluidic device comprising one or more parking loops 12, each parking loop 12 comprising a bypass channel 14 and a lower branch 16 capable of retaining one or more drops, wherein bypass channel 14 has a smaller hydrodynamic resistance than the lower branch 16.

16 Claims, 9 Drawing Sheets

(56) References Cited

U.S. PATENT DOCUMENTS

2010/0163109 A1 7/2010 Fraden et al.
2010/0252118 A1 10/2010 Fraden et al.

OTHER PUBLICATIONS

Teh, S. Y. et al., "Droplet microfluidics", Lab Chip, 2008, 8, 198-220.
Yang, C. G. et al. "Manipulation of droplets in microfluidic systems", TrAC, Trends Anal. Chem., 2010,29, 141-157.
Solvas, X. C. I. et al., "Droplet microfluidics: recent developments and future applications", Chem. Commun., 2011, 47, 1936-1942.
Huebner, A. et al., "Static microdroplet arrays: a microfluidic device for droplet trapping, incubation and release for enzymatic and cell-based assays", Lab Chip, 2009, 9, 692-698.
Schmitz, C. H. J. et al., "Dropspots: a picoliter array in a microfluidic device", Lab Chip, 2009, 9, 44-49.
Shi, W. W. et al., "Droplet-based microfluidic system for individual Caenorhabditis elegans assay", Lab Chip, 2008, 8, 1432-1435.
Li, L. et al., "Nanoliter microfluidic hybrid method for simultaneous screening and optimization validated with crystallization of membrane proteins", Proc. Nat/. Acad. Sci. U. S. A., 2006, 103, 19243-19248.
Liu, W. S. et al., "Isolation, incubation, and parallel functional testing and identification by FISH of rare microbial single-copy cells from multi-species mixtures using the combination of chemistrode and stochastic confinement", Lab Chip, 2009, 9, 2153-2162.
Abate, A. R. et al.,"High-throughput injection with microfluidics using picoinjectors", Proc. Nat/. Acad. Sci. U. S. A., 2010, 107, 19163-19166.
Sun, M. et al., "High-throughput sample introduction for droplet-based screening with an on-chip integrated sampling probe and slotted-vial array", Lab Chip, 2010, 10, 2864-2868.
Du, W. B. et al., "Automated microfluidic screening assay platform based on DropLab", Anal. Chern., 2010, 82, 9941-9947.
Song, H. et al., "Millisecond kinetics on a microfluidic chip using nanoliters of reagents", J. Am. Chern. Soc., 2003, 125, 14613-14619.
Bui, M. N. et al., "Enzyme Kinetic Measurements Using a Droplet-Based Microfluidic System with a Concentration Gradient" Anal. Chem., 2011, 83, 1603-1608.
Damen, N. et al., "Simultaneous measurement of reactions in microdroplets filled by concentration gradients", Lab Chip, 2009, 9, 1707-1713.
Lorenz, R. M. et al., "Simultaneous generation of multiple aqueous droplets in a microfluidic device", Anal. Chim. Acta, 2008, 630, 124-130.
Bithi, S. S. et al, "Behavior of a train of droplets in a fluidic network with hydrodynamic traps", Biomicrofluidics, 2010, 4, 044110-1-10.
Chen, D. L. et al. "Microfluidic cartridges preloaded with nanoliter plugs of reagents: an alternative to 96-well plates for screening" Curr. Opin. Chern. Bioi., 2006, 10,226-231.
Theberge, A. B. et al., "Generation of picoliter droplets with defined contents and concentration gradients from the separation of chemical mixtures", Anal. Chem 2010, 82, 3449-3453.
Zheng, B. et al., "Using nanoliter plugs in microfluidics to facilitate and understand protein crystallization", Curr. Opin. Struct. Bioi., 2005, 15, 548-555.
International Search Report (KIPO) PCT/US2012/036815 Dated Nov. 14, 2012.
Huebner, A. et al., Microdroplets: A sea of applications? Lab on a Chip 8 (8), 1244-1254 (2008).
Song, H. et al., Reactions in droplets in microfluidic channels. Angewwandte Chemie—International Edition 45 (44), 7336-7356 (2006).
Teh, S. Y. et al., Droplet microfluidics. Lab on a Chip 8 (2), 198-220 (2008).
Zheng, B. et al., Screening of protein crystallization conditions on a microfluidic chip using nanoliter-size droplets. Journal of the American Chemical Society 125 (37), 11170-11171 (2003).
Shim, J. U. et al., Using microfluidics to decouple nucleation and growth of protein crystals. Crystal Growth & Design 7 (11), 2192-2194 (2007).
Zhang, Y. H. et al., Microfluidic DNA amplification—A review. Analytica Chimica Acta 638 (2), 115-125 (2009).
Shen, F. et al., Nanoliter Multiplex PCR Arrays on a SlipChip. Analytical Chemistry 82 (11), 4606-4612 (2010).
Beer, N. R. et al, On-chip, real-time, single-copy polymerase chain reaction in picoliter droplets. Analytical Chemistry 79 (22), 8471-8475 (2007).
Mohr, S. et al., Numerical and experimental study of a droplet-based PCR chip. Microfluidics and Nanofluidics 3 (5), 611-621 (2007).
Wang, F. et al., Performance of nanoliter-sized droplet-based microfluidic PCR. Biomedical Microdevices 11 (5), 1071-1080 (2009).
Agresti, J. J. et al., Ultrahigh-throughput screening in drop-based microfluidics for directed evolution (vol. 170, p. 4004, 2010). Proceedings of the National Academy of Sciences of the United States of America 107 (14), 6550-6550 (2010).
Koster, S. et al., Drop-based microfluidic devices for encapsulation of single cells. Lab on a Chip 8 (7), 1110-1115 (2008).
He, M. Y. et al., Selective encapsulation of single cells and subcellular organelles into picoliter- and femtoliter-volume droplets. Analytical Chemistry 77 (6), 1539-1544 (2005).
Kumaresan, P. et al., High-Throughput Single Copy DNA Amplification and Cell Analysis in Engineered Nanoliter Droplets. Analytical Chemistry 80 (10), 3522-3529 (2008).
Brouzes, E. et al., Droplet microfluidic technology for single-cell high-throughput screening. Proceedings of the National Academy of Sciences of the United States of America 106 (34), 14195-14200 (2009).
Kobel, S. et al., Optimization of microfluidic single cell trapping for long-term on-chip culture. Lab on a Chip 10 (7), 857-863 (2010).
Baret, J. C. et al, Quantitative Cell-Based Reporter Gene Assays Using Droplet-Based Microfluidics. Chem. Biol. 17 (5), 528-536 (2010).
Marcoux, P. R. et al., Micro-confinement of bacteria into w/o emulsion droplets for rapid detection and enumeration. Colloid Surf. A—Physicochem. Eng. Asp. 377 (1-3), 54-62 (2011).
Park, J. et al., Microdroplet-Enabled Highly Parallel Co-Cultivation of Microbial Communities. PLoS One 6 (2), e17019 (2011).
Dendukuri, D. et al., Controlled synthesis of nonspherical microparticles using microfluidics. Langmuir 21 (6), 2113-2116 (2005).
Dendukuri, D. et al., The synthesis and assembly of polymeric microparticles using microfluidics. Advanced Materials 21, 1-16 (2009).
Shestopalov, I. et al., Multi-step synthesis of nanoparticles performed on millisecond time scale in a microfluidic droplet-based system. Lab on a Chip 4 (4), 316-321 (2004).
Shah, R. K. et al., Designer emulsions using microfluidics. Materials Today 11, 18-27 (2008).
Thorsen, T. et al., Dynamic pattern formation in a vesicle-generating microfluidic device. Physical Review Letters 86 (18), 4163-4166 (2001).
Bithi, S. S. et al., Behavior of a train of droplets in a fluidic network with hydrodynamic traps. Biomicrofluidics 4 (4), 10 (2010).
Xia, Y. N. et al., Soft lithography. Annual Review of Materials Science 28, 153-184 (1998).
Sun, M. et al., Microfluidic static droplet arrays with tuneable gradients in material composition. Lab Chip 11, 3949-3952 (2011).
Nie, Z. et al., Janus and ternary particles generated by microfluidic synthesis: Design, synthesis and self-assembly. Journal of American Chemical Society 128, 9408-9412 (2006).
Christopher, G. F. et al., Microfluidic methods for generating continuous droplet streams. J Phys D Appl Phys 40 (19), R319-R336 (2007).
Anna, S. L. et al., Formation of dispersions using "flow focusing" in microchannels. Applied Physics Letters 82 (3), 364-366 (2003).

(56) References Cited

OTHER PUBLICATIONS

Tan, W. H. et al., Monodisperse alginate hydrogel microbeads for cell encapsulation. Advanced Materials 19 (18), 2696-+ (2007).
Um, E., et al., Random breakup of microdroplets for single-cell encapsulation. Applied Physics Letters 97 (15) (2010).

METHODS AND DEVICES TO CONTROL FLUID VOLUMES, REAGENT AND PARTICLE CONCENTRATION IN ARRAYS OF MICROFLUIDIC DROPS

CROSS-REFERENCE TO RELATED APPLICATIONS

This application claims priority to, and is the National Stage of International Application No. PCT/US2012/036815 filed on May 7, 2012 and claims the priority of U.S. Provisional Patent Application Ser. No. 61/604,785, filed on Feb. 29, 2012 and U.S. Provisional Patent Application Ser. No. 61/483,087, filed on May 6, 2011, the contents of which are incorporated by reference herein in their entirety.

STATEMENT OF FEDERALLY FUNDED RESEARCH

This invention was made with U.S. Government support under Contract No. CA-135862, awarded by the National Institutes of Health. The government has certain rights in this invention.

TECHNICAL FIELD OF THE INVENTION

The present invention relates in general to the field of microfluidics, and more particularly, to methods and devices to control fluid volumes, reagent concentration, and particle concentration in arrays of microfluidic drops.

BACKGROUND ART

Without limiting the scope of the invention, its background is described in connection with microfluidic structures. Current industry approaches for arraying fluid volumes involve expensive methods such as robotic dispensing in micro-scale multi-well plates or spotting of fluids on substrates. These approaches suffer from using microliter-scale fluid volumes, and are also not amenable to further reduction in fluid volumes due to liquid evaporation. Moreover, these approaches do not allow isolation and study of individual cells, which is important in applications such as cancer and bacterial infections, where there is a need to identify the 'rogue' cells among a population.

Droplet-based microfluidics has the potential to offer flexible and cheaper approaches to alleviate the problems associated with current robotic dispensing systems. Recent advances in droplet-based microfluidics[1-3] have provided a unique paradigm to compartmentalize reactions in very small volumes for applications ranging from biomolecule analysis[4-11] to cell-based assays[12-21] to fabrication of novel materials[22-26]. Monodisperse nanoliter- to picoliter-scale drops can be rapidly generated in an immiscible carrier phase using pressure-driven flows in microfluidic devices[27-29]. Additional benefits of such droplet-based microfluidics include the ability to isolate single biomolecules or cells in drops and minimize product dispersion during a reaction. There remains, however, a need for structures and methods that allow for isolation and study of, e.g., individual cells or biomolecules.

SUMMARY OF THE INVENTION

One embodiment of the present invention includes a microfluidic device comprising: a substrate comprising an inlet and an outlet connected to a main conduit; one or more parking loops 12 connected to the main conduit, each parking loop 12 comprising a bypass channel 14 and a lower branch with a fluidic trap 16 capable of retaining one or more drops, wherein the bypass channel 14 has a smaller hydrodynamic resistance than the lower branch 16 with a fluidic trap 16.

The device in some embodiments may include a cartridge connected to the inlet, wherein a sample slug can be introduced into the main conduit and into the fluidic trap 16. The device in some embodiments may include a hydrodynamic resistance ratio between the lower branch and bypass channel that ranges from 1.0 to 2.0. For example, the hydrodynamic resistance ratio can be 1.1, 1.2, 1.3, 1.4, 1.5, 1.6, 1.7, 1.8, 1.9 or 2.0. The hydrodynamic resistance ratio between the lower branch and bypass channel is preferably from 1.4 to 1.6. For example, it can be 1.4, 1.5, or 1.6. The device in some embodiments may include a fluid that is at least partially aqueous. The device in some embodiments further comprises an array of parking loops formed into at least one of a square array, a triangular array, a pentagonal array, a hexagonal array, a rectangular array, a polygonal array, a circular array, an oval array, an undular array, or a three-dimensional array. The device in some embodiments may include a reagent drop that is introduced into the bypass channel to control the passage of one or more water droplets. The device in some embodiments is adapted to separate blood or other cells. In some embodiments, the parking loop has a volume of 1 to 1,000 nL. For example, its volume can be 1, 5, 10, 15, 20, 25, 30, 50, 75, 100, 125, 150, 200, 250, 500, 750 or 1,000 nL.

One embodiment of the present invention includes a method of making a microfluidic device comprising the steps of forming in a substrate an inlet and an outlet connected to a main conduit and one or more parking loops 12, each parking loop 12 comprising a bypass channel 14 and a lower branch with a fluidic trap 16 capable of retaining one or more drops, wherein the bypass channel 14 has a smaller hydrodynamic resistance than the lower branch with a fluidic trap 16. The method in some embodiments may include a device having a hydrodynamic resistance ratio between the lower branch and bypass channel ranging from 1.0 to 2.0. For example, the hydrodynamic resistance ratio can be 1.1, 1.2, 1.3, 1.4, 1.5, 1.6, 1.7, 1.8, 1.9 or 2.0. The hydrodynamic resistance ratio between the lower branch and bypass channel is preferably from 1.4 to 1.6. For example, it can be 1.4, 1.5, or 1.6. The method in some embodiments may include a device having an array of parking loops formed into at least one of a square array, a triangular array, a pentagonal array, a hexagonal array, a rectangular array, a polygonal array, a circular array, an oval array, an undular array, or a three-dimensional array. The method in some embodiments may include a device adapted to separate blood or other cells.

One embodiment of the present invention includes a method of transporting drops, cells, or compositions and forming a droplet-based concentration gradient in solution through a microfluidic device by providing a first cartridge comprising a sample solution comprising one or more drops, cells, or compositions; connecting the first cartridge to an inlet of an microfluidic device, wherein the microfluidic device comprises an inlet in fluid communication with one or more conduits, connecting them to the one or more parking loops 12, each parking loop 12 comprising a bypass channel 14 and a lower branch with a fluidic trap 16 capable of retaining one or more drops, wherein the bypass channel 14 has a smaller hydrodynamic resistance than the lower branch with a fluidic trap 16 and providing in fluid communication one or more outlets from the bypass channel; and filling the fluidic trap 16 with at least a portion of the sample solution.

The method in some embodiments may further comprise the step of connecting a diluting cartridge to the inlet to form a gradient slug from a gradient droplet array, wherein the gradient slug gets more concentrated as it travels past each fluidic trap 16 due to exchanges taken away from each fluidic trap by the gradient slug, wherein the highest concentration is at a gradient slug front, and a lowest concentration is at a gradient slug tail. In some embodiments the method may include a device adapted to separate blood or other cells. In some embodiments the solution does not include a surfactant. In some embodiments the method may include a device adapted to separate blood or other cells. The hydrodynamic resistance ratio between the lower branch and bypass channel is from 1.0 to 2.0; for example: 1.1, 1.2, 1.3, 1.4, 1.5, 1.6, 1.7, 1.8, 1.9 or 2.0. The hydrodynamic resistance ratio between the lower branch and bypass channel is preferably from 1.4 to 1.6; for example: 1.4, 1.5, or 1.6. In some embodiments the method may include a fluid in the device that is at least partially aqueous. In some embodiments the method may include a device having an array of parking loops. The array of parking loops is formed into at least one of a square array, a triangular array, a pentagonal array, a hexagonal array, a rectangular array, a polygonal array, a circular array, an oval array, an undular array, or a three-dimensional array. The array of parking loops is in series and provides for serial dilution of the drops, cells, or compositions in the solution. The reagent drop is stored in the trap so that reagent transfer can occur from the passage of one or more water droplets into the bypass channel. The solution is at least partially aqueous. The array of parking loops is incorporated into a long plug gradient. The one or more parking loops can be in fluid communication with one or more of the following possible additional reservoirs: cartridges, mixing tubes, concentrator arrays, conduits, outlets, reagent reservoirs, valves, particle segregators, filters, plugs, or pumps.

DESCRIPTION OF THE DRAWINGS

For a more complete understanding of the features and advantages of the present invention, reference is now made to the detailed description of the invention along with the accompanying FIGURES and in which:

FIG. 7A is an image illustrating the concept of dilution; FIG. 7B is an image of a time sequence of snapshots showing the reduction in concentration of the reagent in the parked drop due to sequential removal of reagent from the parked drop by moving water drops; FIG. 7C is a graph of the concentration profile of the reagent in moving drops.

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Despite the attractive attributes of microfluidic drops, flexible methods are lacking that can: (i) generate immobilized arrays of microfluidic drops of uniform or gradually varying size on substrates, so that reaction products can be observed in individual drops over a long duration; (ii) control the concentration of one or many reagents in individual drops over a wide range for applications in high throughput screening; and (iii) manipulate the concentration of insoluble particles (e.g. beads, bacteria, mammalian cells or small organisms) in individual drops, in addition to removing or adding particles.

Figure 1:
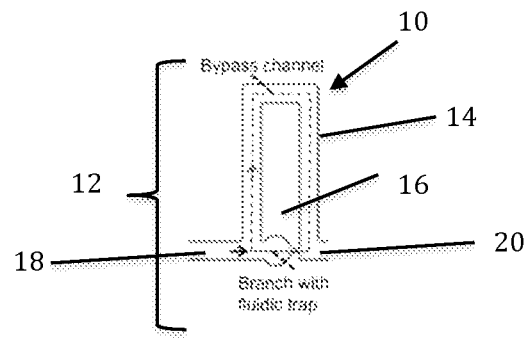
FIG. 1 is a schematic of a microfluidic parking loop. The parking loop consists of an upper branch referred to as a bypass channel, and a lower branch containing a fluidic trap.

This invention includes new methods and devices that allow significant control over the issues discussed in items (i-iii) above. The microfluidic parking network (MPN) 10 includes at least one parking loop 12 (see FIG. 1). Each parking loop 12 has a bypass channel 14 (upper branch) and a lower branch 16 that can park (i.e. trap) drops (not depicted). The design of the bypass channel 14 has a smaller hydrodynamic resistance than the lower branch with a fluidic trap 16, and the ratio of their hydrodynamic resistance is, e.g., 1.5 (see below for additional details on the device design and fabrication). A fluid, solvent, solution and/or bubble, drop, cell or composition enters the parking loops through an inlet 18 and has an outlet 20.

The present inventors found that the microfluidic drop dynamics in the MPNs disclosed herein have a novel mechanism called hydrodynamic self-rectification that allows moving drops to momentarily merge with stationary drops and detach, leaving the volumes of both the moving and stationary drops unchanged. The self-rectification mechanism enables: the generation of exceptionally uniform immobilized nanoliter-scale drops in microfluidic substrates. These static droplet arrays (SDAs) can be generated over a broad range of flow rates, with throughput at least ten times compared to earlier approaches. The method is also very flexible because uniform arrays of controlled volumes can be generated by simply changing the size of the mechanical obstacle (i.e. trap). In some applications, it is desirable to array fluids with gradually varying volumes, so that the number of target species encapsulated can be incrementally varied or to allow readouts from assays that have a large dynamic range. The proposed mechanism (which is not a limitation of the present invention) of self-rectification also enables robust formation of SDAs containing gradually varying fluid volumes. When arraying fluid volumes, some applications demand that fluids of distinct composition are simultaneously immobilized, to enable faster throughput. It is shown herein that this multiplexing capability can be easily achieved using our self-rectification mechanism. In high throughput screening applications, a sample is often tested with one or more reagents over a wide range of concentration to identify the optimal target concentration (e.g. drug screening). Therefore, the self-rectification mechanism was demonstrated using soluble reagent concentration that can be manipulated in a facile manner, enabling rapid dilutions with nanoliter fluid volumes. It was also demonstrated that in addition to the concentration of soluble reagents, the amount of insoluble particles (e.g. beads, bacteria, mammalian cells and small organisms) per drop can also be controlled.

Static Droplet Arrays of Exceptional Uniformity.

Arrays of nanoliter-to-picoliter-scale drops immobilized at prescribed coordinates on substrates provide a powerful means to monitor individual reactions in many drops simultaneously. Current approaches to producing these static droplet arrays (SDAs) often require simultaneous optimization of drop production (e.g. drop size and spacing), surfactant concentration (e.g. to avoid drop coalescence), obstacle geometry (e.g. trap size, groove width), network architecture (e.g. placement of traps/grooves) and flow conditions (e.g. to prevent drop dislodging). This invention addressed the need for flexible methods that do not require extensive optimization of system parameters to generate SDAs. The present hydrodynamic self-rectification of the present invention allows for the production of monodisperse SDAs that do not require surfactant, or precise tuning of drop size, trap size, or drop spacing in the network.

Figure 2:
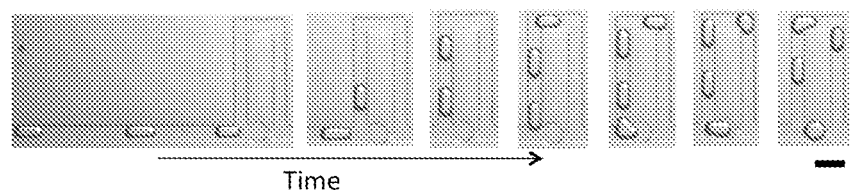
FIG. 2 is an image of the time-sequence images of the process of droplet parking in the fluidic traps.

The basic principle for drop trapping in MPNs with surfactant-coated (or non-coalescing) drops has been described previously[30, 31]. As shown in FIG. 2, if the hydrodynamic resistance of the bypass channel is lower, drops initially choose the bypass. When a specified number of drops are present in the bypass, the hydrodynamic resistance of the bypass channel is elevated causing reduction in the carrier fluid flow rate. If the carrier fluid flow rate reduces by sufficient amount, then the subsequent drop enters the fluidic trap and is parked.

Figure 3:
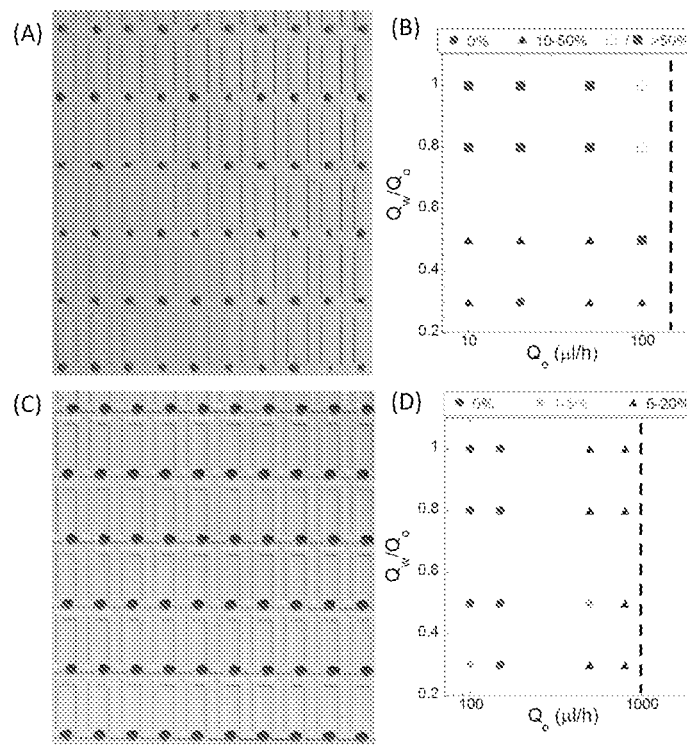
FIG. 3A is an image showing a static drop array with surfactant-coated drops showing the variability in trapped drop volumes.
FIG. 3B is a diagram in which one flow condition shows zero polydispersity, and all other flow conditions yield arrays with significant polydispersity.
FIG. 3C is an image of the static drop array without any surfactant added to the drops showing the highly uniform array.
FIG. 3D is a diagram in which several of the flow conditions yield monodisperse static drop arrays.

However, the above approach as we show in FIG. 3A, B is not very flexible. To illustrate the lack of flexibility, we introduced 2 wt % surfactant-coated drops into the MPN at varying drop size and spacing by controlling the water flow rate ($Q_w$) and carrier fluid flow rate ($Q_o$) at a microfluidic T-junction. As shown in FIG. 3B, we find that at only one flow condition of $Q_o=20$ µL/hr and $Q_w/Q_o=0.3$, the SDA is monodisperse as indicated by the calculated polydispersity index (the polydispersity index is defined as the percentage of drops that do not fill traps uniformly). We observe that at all other explored flow conditions, the polydispersity index is much greater than zero, implying that the trapped volumes have a high degree of non-uniformity (see FIG. 3B). At $Q_o>100$ µL/hr, drops squeeze through the traps, precluding formation of a uniform static drop array.

FIG. 2 shows time-sequence images of the process of droplet parking in the fluidic traps. The ratio of hydrodynamic resistance of the lower channel to bypass is 1.5.

Schematic of a Microfluidic Parking Loop.

The parking loop consists of an upper branch referred to as bypass channel, and a lower branch containing a fluidic trap. Flow conditions are $Q_o=20$ μL/hr and $Q_w/Q_o=0.3$. Scale bar is 500 μm.

When we introduced drops that do not contain any added surfactant into MPNs, we unexpectedly found that the static drop array is exceptionally uniform (see FIG. 3C, D). Moreover this uniformity is obtained over a broad range of flow conditions, as shown in FIG. 3D. Interestingly, the flow condition at which drops squeeze through the traps is also pushed to ten times higher flow rate, implying that the static drop array can be generated in less time, enabling higher throughput of drop immobilization.

FIGS. 3A to 3D show the operation of the present invention. FIG. 3A is an image showing a static drop array with surfactant-coated (non-coalescing) drops showing the variability in trapped drop volumes. FIG. 3B is a diagram where only one flow condition shows zero polydispersity, and all other flow conditions yield arrays with significant polydispersity. FIG. 3C is an image of the static drop array without any surfactant added to the drops showing the highly uniform array. FIG. 3D is a diagram in which several flow conditions yield monodisperse static drop arrays.

The basic mechanisms underlying the formation of these exceptionally uniform nanoliter droplet arrays are two fold. As shown in FIG. 4A, we find that whenever a trap is overfilled, we find the moving drops coalesce with the trapped drop, rectifying the trapped volume. Likewise, as shown in FIG. 4B, when the trap is underfilled, even in this case, the moving drops coalesce and detach, removing the excess fluid volume, thereby rectifying the trapped volume. These two 'hydrodynamic self-rectification' events are the main reason for the formation of exceptionally uniform trapped volumes in MPN. Further investigation revealed that as long as the drop size in the train is greater than the trap size, the self-rectification mechanism persists, causing SDAs of high monodispersity.

Figure 4:
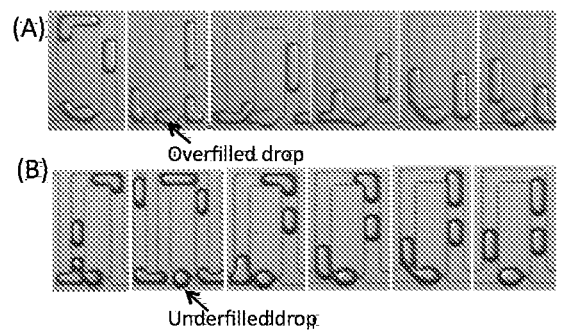
FIG. 4A is an image of the time-sequence snapshots showing an overfilled trapped volume being rectified by coalescence of the moving drop with the parked drop.
FIG. 4B is an image of the time-sequence snapshots showing an underfilled trapped volume being rectified by coalescence of the moving drop with the parked drop.

FIG. 4 shows the effect of overfilling and underfilling. FIG. 4A is a time-sequence snapshots showing an overfilled trapped volume being rectified by coalescence of the moving drop with the park drop. FIG. 4B is a time-sequence of snapshots showing an underfilled trapped volume being rectified by coalescence of the moving drop with the parked drop.

Static Droplet Arrays of Gradually Varying Volumes.

Figure 5:
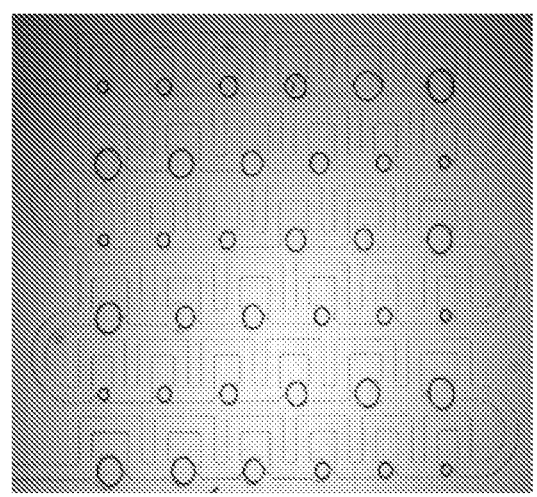
FIG. 5 is an image of the static drop array with gradually varying volumes obtained by hydrodynamic self-rectification of surfactant-free drops.

To immobilize drops of gradually varying volumes, an MPN was designed, where the trap size is increasing to accommodate volumes ranging from 5 nL-25 nL (see FIG. 5). When a train of drops without surfactant was introduced, it was found that the hydrodynamic self-rectification mechanism comes into operation and fixes any underfilled or overfilled trap, leading to full occupation of the trap volume.

FIG. 5 shows the static drop array with gradually varying volumes obtained by hydrodynamic self-rectification of surfactant-free drops. The drop volume varies from 5-25 nanoliters.

Static Droplet Arrays of Different Composition.

Figure 6:
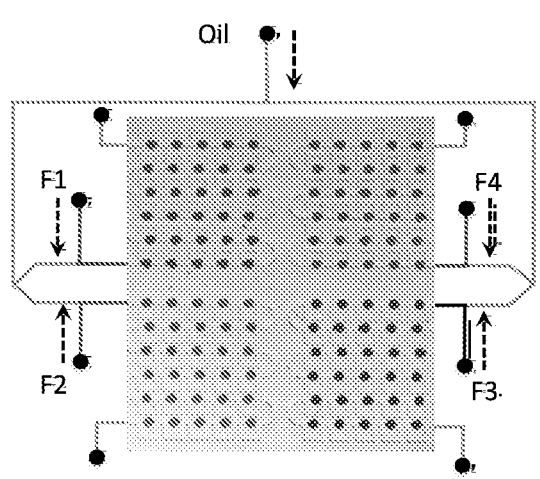
FIG. 6 is an image of static drop arrays with simultaneous immobilization of fluid volumes of different composition in a multiplexed microfluidic parking network.

To immobilize drops of different composition, we designed an MPN, which consists of one inlet for carrier fluid flow that splits into four branches, as shown in FIG. 6. In this design, four individual inlets deliver the different aqueous fluids. Using this device strategy, we are able to simultaneously generate multiplexed arrays of different reagent composition.

FIG. 6 is one example of a static drop array with simultaneous immobilization of fluid volumes of different composition in a multiplexed microfluidic parking network. A single inlet for oil flow feeds four arrays. F1-F4 represent the four different aqueous fluids injected into the network.

Serial Dilutions in Mobile Droplet Arrays.

In the hydrodynamic self-rectification mechanism, the moving drop collides with the parked drops, momentarily coalesces and then detaches, leaving the volumes of both the moving and parked drops unchanged. During the process of coalescence, fluid from the parked drop transfers to the moving drop and vice versa. We harnessed this insight to conduct serial dilutions in microfluidic drops, which are essential to high throughput screening.

FIGS. 7A to 7C show drop dilution using a single microfluidic parking loop. FIG. 7A is a schematic illustrating the concept of dilution. FIG. 7B is a time sequence of snapshots showing the reduction in concentration of the reagent (black dye) in the parked drop due to sequential removal of reagent from the parked drop by moving water drops. FIG. 7C is a graph of the concentration profile of the reagent in moving drops.

Figure 7:
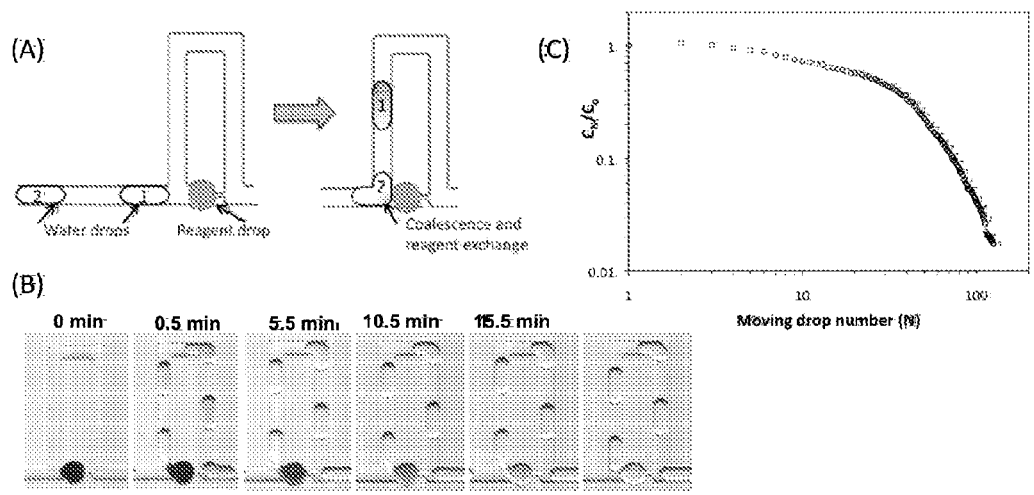
FIG. 7 depicts drop dilution using a single microfluidic parking loop.

To demonstrate serial dilution, a drop containing a reagent was parked (black food-color dye), and then introduced a train of water drops. As shown in FIG. 7, the water drops coalesce with the reagent-loaded drop, removing material from the parked drop. Since material is removed after every collision event, over time, the concentration of the reagent in the parked drop is reduced. This would imply that the moving drops contain a sequential variation of reagent from drop-to-drop with the first drop containing the highest reagent concentration and the last drop in the array containing the least reagent concentration (see FIG. 7C).

Figure 8:
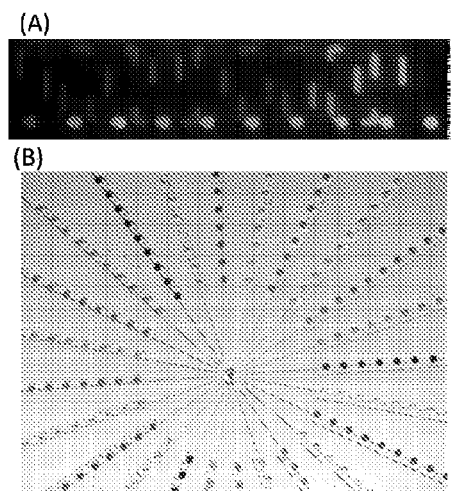
FIG. 8A is an image showing a drop dilution using multiple microfluidic parking loops.
FIG. 8B is an image showing a radially arranged multiplexed microfluidic parking network, with one suction port (in the center) and several (24) inlet ports to accomplish generation of static drop arrays of 24 different compositions.

Additional flexibility over the variation in reagent concentration can be achieved by including multiple loops as shown in FIG. 8A. Finally, the method is amenable to multiplexing, where dilution of several test samples can be performed simultaneously (see FIG. 8B).

FIGS. 8A and 8B show drop dilution. FIG. 8A is an image showing drop dilution using multiple microfluidic parking loops. Reagent (fluorescent dye) concentration variation is observed in both the stationary and moving drops. FIG. 8B is an image showing a radially arranged multiplexed microfluidic parking network with one suction port (in the center) and several (24) inlet ports to accomplish generation of static drop arrays of 24 different compositions.

It was found that this method is very powerful because reagent concentration in drops can be varied over a wide range that is limited only by the detection technique. Although we harness flow-induced coalescence to merge the moving and parked drop, electric fields can also be used (by embedding electrodes on the chip) to induce on-demand coalescence, enabling full control over which moving drop exchanges reagents with the parked drop.

Figure 9:
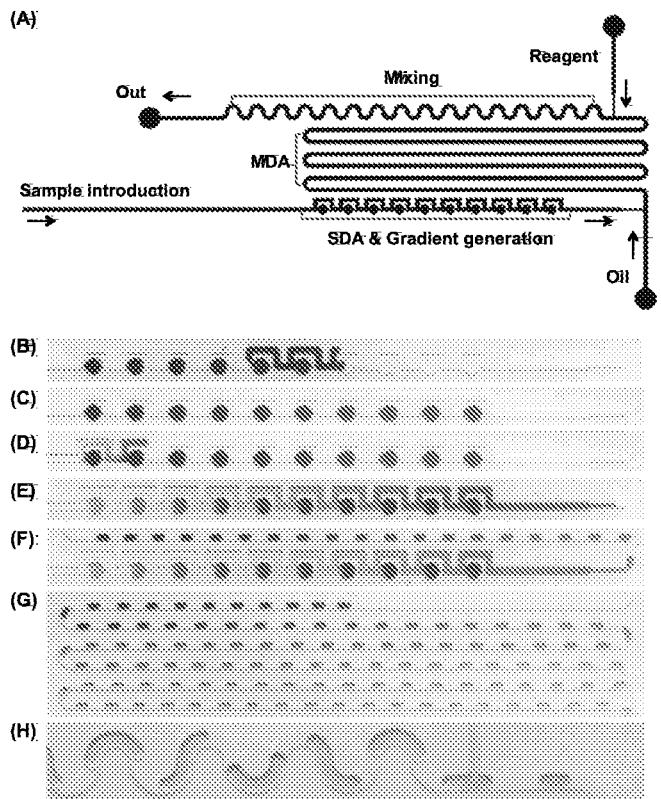
FIG. 9A is a schematic of the device design that generates moving drop arrays with variation in reagent concentration by fragmentation of a long plug containing a gradient in reagent concentration.
FIG. 9B is an introduction of the reagent plug into an array with ten traps.
FIG. 9C is an image of the formation of an array of ten trapped reagent volumes of homogeneous composition.
FIG. 9D shows the introduction of a long water plug that removes reagent from the parked drops.
FIG. 9E illustrates a reagent gradient is established in the long water plug due to repeated removal of reagent from the trapped volumes.
FIG. 9F illustrates a plug with reagent gradient is chopped by introducing oil orthogonally to the trapping array.
FIG. 9G illustrates an image revealing the gradient in reagent concentration in moving drops.
FIG. 9H illustrates the downstream introduction of a different reagent into the array of moving drops already containing a concentration gradient.

In another variant of the above method, we create a concentration gradient of reagent in a long plug and subsequently fragment the plug into smaller droplets to produce moving droplet arrays with variation in individual reagent concentration (see FIG. 9). The steps in this method are the following: a long reagent plug is introduced into the device, so as to generate several trapped volumes of uniform composition; a water (i.e. diluting) plug is introduced that sequentially removes reagent from the trapped drops, generating a concentration gradient in the moving plug as shown in FIG. 9D, E; the diluting plug, which becomes a long gradient plug, is then chopped into a plurality of drops (or smaller plugs) by pumping oil through the side channel, thereby creating drops at the T-junction (FIG. 9F). The longitudinal concentration gradient present in the long plug is now converted into discrete variation in reagent concentration from drop-to-drop as shown in FIG. 9G. Additional materials (e.g. soluble reagents or cells) can be introduced into the reagent-loaded drops further downstream (FIG. 9H).

FIGS. 9A to 9H show various steps in the method. FIG. 9A is a schematic of the device design that generates moving drop arrays with variation in reagent concentration by fragmentation of a long plug containing a gradient in reagent concentration. FIG. 9B shows the introduction of the reagent plug into an array with ten traps. FIG. 9C shows the formation of an array of ten trapped reagent volumes of homogeneous composition. FIG. 9D shows the introduction of a long water plug that removes reagent from the parked drops. FIG. 9E illustrates an example where a reagent gradient is established in the long water plug due to repeated removal of reagent from the trapped volumes. In FIG. 9F, the plug with reagent gradient is chopped by introducing oil orthogonally to the trapping array. FIG. 9G is an image revealing the gradient in reagent concentration in moving drops. FIG. 9H illustrates a downstream introduction of a different reagent into the array of moving drops already containing a concentration gradient.

The gradient in reagent concentration between drop-to-drop in this method can be tuned by a number of parameters including number and size of traps, volume of the long diluting plug, the flow rate of the carrier fluid pushing the long diluting plug, flow rate of the carrier fluid in the side arm of the T-junction that fragments the long plug, and initial concentration of the reagent in the trapped drops.

Gradient in Particle Concentration in Microfluidic Droplet Arrays.

Figure 10:
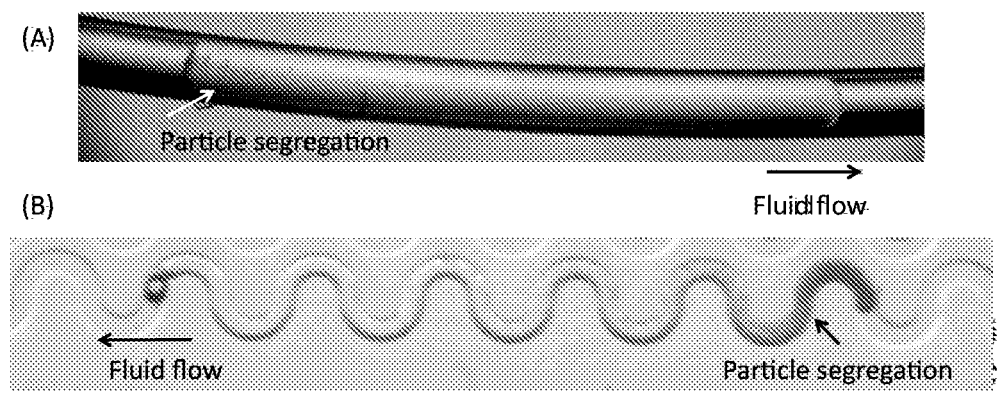
FIG. 10A is an image of the segregation of 15 micron particles in a water plug surrounded by mineral oil when flowing through a narrow tubing of inner diameter 200 µm.
FIG. 10B is an image showing a concentration of 10 micron particles towards the back-end of the water plug flowing through a serpentine microchannel of width 200 µm. Flow rate is 0.5 µL/min.

It was found that when an aqueous plug containing a suspension of particles was aspirated into a narrow tubing prefilled with oil, the particles tend to segregate and collect at the tail end of the moving aqueous plug (FIG. 10A). The mechanism causing this segregation is probably due to the transport of the particles by the recirculating flow inside the drop, with subsequent entrapment of the particles by the vortex flow in the tail end of the plug$_{32}$. We find that the particle segregation persists even when the immiscible plug is injected into a serpentine channel as shown in FIG. 10B.

FIGS. 10A and 10B show the gradient in particle concentration in microfluidic droplet arrays: FIG. 10A illustrates the segregation of 15 micron particles in a water plug surrounded by oil (mineral oil) when flowing through a narrow tubing of inner diameter 200 µm. FIG. 10B illustrates the concentration of 10 micron particles towards the back-end of the water plug flowing through a serpentine microchannel of width 200 µm. Flow rate is 0.5 µL/min.

Figure 11:
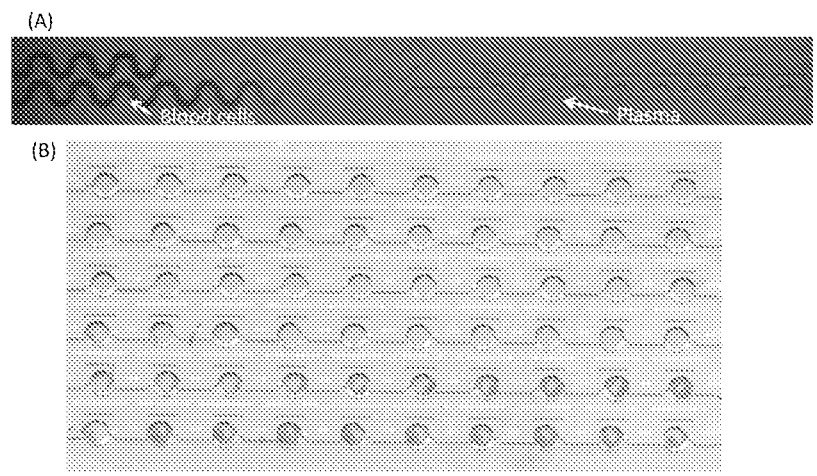
FIG. 11A is an image of the segregation of blood cells towards the back-end of the plug, which is flowing through a channel of width and height 200 µm.
FIG. 11B illustrates static arrays in which drops at the beginning of the array contain particles whereas those at the end of the array are devoid of the particles. Flow rate is 0.5 µL/min.

In FIG. 11A, the particle segregation method allows one to separate blood cells from whole blood yielding high purity plasma (the clear fluid). This particle segregation principle, when coupled to our microfluidic parking network, allows one to park droplets containing particles and those that are devoid of particles. Note that because the particles (or cells) are at the back-end of the plug, they are encapsulated in drops at the beginning of the array, whereas the drops at the end of the array contain clear fluid. These results are particularly useful in applications where there is a need to analyze biomarkers in plasma. This approach is also an efficient means to concentrate cellular suspensions.

FIGS. 11A and 11B show the particle separation method. FIG. 11A is an image of the segregation of blood cells towards the back-end of the plug, which is flowing through a channel of width and height 200 µm. FIG. 11B shows static arrays in which drops at the beginning of the array contain particles whereas those at the end of the array are devoid of the particles. Flow rate is 0.5 µL/min. Solution of black dye (McCormick) was diluted 20× by distilled water before use. Mineral oil (Sigma-Aldrich) was used as carrier fluid.

Device Fabrication.

Standard photolithography procedures were used to generate a mold (SU-8 2100, MicroChem) with uniform feature height of 200 µm$_{33}$. Devices were fabricated by pouring polydimethylsiloxane (PDMS) on the mold with subsequent curing. The PDMS replicas were bonded to another flat PDMS substrate using plasma treatment. The surface of the channels was modified by treatment with Aquapel (PPG Industries) followed by drying with air.

Device Design.

In one embodiment, the main channels were 200 µm in width. The diameters of the trap were either 450 or 320 µm. The hydrodynamic resistance ratio ($R_T/R_B$) of the lower branch ($R_T$) and bypass channel ($R_B$) was between 1.5-3.2. Drops were either generated by using a microfluidic T-junction$_{31}$ or injected using the cartridge method$_{34}$.

Microfluidic Studies.

Syringe pumps (PHD2000, Harvard Apparatus, USA) and syringes (Gastight 1710, Hamilton, USA) were employed to drive the liquids. A PTFE Tubing (203 µm i.d., 356 µm o.d., Zeus, USA) was used as a cartridge to supply samples to the microfluidic device. Experiments were conducted under a stereo microscope (SZX16, Olympus, Japan). Multipage TIFF files were recorded by a high speed imager (pco. 1200 s, PCO, Germany), and movies were filmed by a CCD camera (StreamView-LR, SVSi, USA). Both the capillary number and Reynolds number are less than 0.005.

Concentration Measurement.

The relative grey-scale intensities of droplets were analyzed in a MATLAB routine. Concentration was determined by measuring the grey-scale intensity of a small region within the drop with respect to the background intensity.

It is contemplated that any embodiment discussed in this specification can be implemented with respect to any method, kit, reagent, or composition of the invention, and vice versa. Furthermore, compositions of the invention can be used to achieve methods of the invention.

In recent years, droplet-based microfluidics has attracted great interest due to the ease in production of tiny droplet microreactors in a sample/reagent-economic way. It is suitable for performing high throughput screening analysis, where numerous kinds of targets are required to be screened.

The multi-well plate is one of the commonly used tools in screening assays, and it is featured as an array of addressable wells in a plate. Droplet microfluidics could bring its consumption scale from the µL scale down to nL scale. The major difference would be that most of the droplets would be generated within a flowing channel rather than by individual injection from above. Although droplets have already been confined inside addressable hydrodynamic traps in a microfluidic chip, there are few reports on replacing components in the trapped droplets or generating a concentration gradient in such an array.

It is significant to generate a droplet array with different compositions or concentration gradient in a droplet-based screening assay. A few works in the prior art have reported the ability to inject different samples or reagents into droplets so far but for a single screen target. However, a concentration gradient with 5-order span in magnitude is still on demand in a preliminary screening assay.

A droplet-based concentration gradient could be achieved either by adjusting the flow rate of each reagent or by employing diffusion and dispersion of the aqueous phase in μm-scale channels to first give the aqueous phase a concentration gradient, then cutting the aqueous phase into dispersed droplets by using a flow of oil downstream of the microluidic chip. However, their gradients in initial experiments were limited to 3-4 orders of magnitude in concentration due to the geometry of the chips.

The droplets trapped into a hydrodynamic trap array were provided by a T-junction generator. The sizes of the trapped droplets fluctuated, and they were closely influenced by the flow rates of aqueous and oil phases. Here we used a cartridge as the sample provider to introduce a long aqueous slug into a microfluidic chip and made the slug divided into uniform droplets by hydrodynamic traps. The traps were fully occupied by the aqueous droplets and the fluctuation caused by T-junction was eliminated. We then infused a secondary diluting slug to the droplets array. The diluting slug contacted each of the trapped droplets, and the rupture of the oil film between the two aqueous liquids led to fusion, diffusion and a serial dilution of the pre-trapped droplets one by one as the slug passed. This finally resulted in the generation of a gradient droplet array. The diluting slugs were preloaded and separated by oil in the cartridge. The range of a concentration gradient could be tuned by the volume, the flow rate, or the number of the diluting slugs, which make this technique much more permissive to get a desired gradient without the limitation of the chip geometry. We demonstrated the technique by diluting dyes, and generating concentration gradients with trapped beads in droplets.

Solutions of black, blue and yellow dyes were diluted 20× by water. 2%, 0.5%, 0.1% and 0% (w/v) Span 80 (Fiuka) in mineral oil (Sigma-Aldrich) were used as oil carrier. 10-3-10-8 M standard solutions of fluorescein sodium salt (Sigma-Aldrich) were freshly prepared in water before experiment. Precision size standard (15.0 μm, Polysciences, Inc., PA, USA) was diluted SOX to get a particle density about 105 beads/ml. Distilled water was used.

A PTFE Tubing (203 μm i.d., 355 μm o.d., Zeus, SC, USA) was used as cartridge to supply samples to microfluidic chip through a Tygon tubing (250 μm i.d., 760 μm o.d., Saint-Gobain, Ohio, USA) and a syringe (Gastight 1710, Hamilton, Nev., USA) on syringe pump (PHD2000, Harvard Apparatus, USA). Cameras (StreamView-LR, SVSi, AL, USA; PL-B776F, PixeLINK, Ottawa, Canada), stereo microscope (SZX16, Olympus, Japan), and inverted fluorescence microscope (IX71, Olympus, Japan) were used to record the experiments.

Chip Fabrication.

Negative photoresist (SU-8 2100, MicroChem, MA, USA) was photolithographically patterned on a silicon wafer to make a mold with height and width about 200 μm. The mold was exposed to a (Tridecafluoro-1,1,2,2-Tetrahydrooctyi)-1-Trichlorosilane (UCT) atmosphere for 2 h to facilitate removing PDMS from the mold afterwards. Degassed polydimethylsiloxane (PDMS) prepolymer mixed with its crosslinker at 10:1 weight ratio was then poured onto the mold before being cured in an oven at 65° C. for 2 h. The cured PDMS replica was peeled off from the mold, access holes were punched, and subjected to a 90 s oxygen plasma treatment with another flat PDMS substrate, and both were bonded together to form the final chip. The dimensions of the hydrodynamic trap were as previously described. To chemically modify the chip, the microfluidic channels were treated with Aquapel (PPG Industries, PA, USA) followed by drying with air. This treatment ensured that the aqueous phase did not adhere to the surface.

The PDMS chip was cut across the main channel and filled with mineral oil through a waste port. The syringe and the connect tubing were also filled with oil without any bubbles inside. We arranged the syringe onto the syringe pump and set the flow rate or target volume. We aspirated the desired slugs into the cartridge sequentially with oil separated each other. The cartridge was then plugged into the main channel from the cross section of the chip. We fixed the chip under the view field of microscope. We started the pump, and then the first slug in the cartridge was infused into the chip and divided into uniform droplets by hydrodynamic traps. We infused the subsequent slug(s) and diluted the trapped droplets.

Design of the Hydrodynamic Trap.

In this work, we used the hydrodynamic traps to trap droplets into an array by using restriction channels. First, we considered the resistance required for confining each droplet in the static traps. There are two flow paths in each trapping unit, which are defined as the upper branch and the lower branch. The ratio of their resistances RL/Ru (lower/upper) was determined by the dimensions of the hydrodynamic trap. In one embodiment, we chose an RL/Ru ratio of about 3 to help prevent undesirable gas bubbles or tiny aqueous droplets from entering and occupying the trap. The trap dimensions were then calculated using the exact analytical solution of Poiseuille flow in a rectangular channel along each path as shown below, where L, h and w are the length, height and width of the channel respectively; μ is the viscosity of oil.

$$R = \frac{12\mu L}{h^3 w}\left[1 - \sum_{n,odd}^{\infty} \frac{1}{n^5} \times \frac{192}{\pi^5} \cdot \frac{h}{w}\tanh\left(\frac{n\pi w}{2h}\right)\right]^{-1}$$

As this RL/Ru and using mineral oil as the carrier fluid, a flow rate of 4 μL/min led to uneven trapping because the front of aqueous plug traveled so quickly that it blocked the lower path before the trap was fully occupied. The trapped droplet could even squeeze through the restriction channel at flow rate of 8 μL/min. Therefore, for these particular device dimensions, we manipulated the fluids for trapping and diluting so that their flow rates were no more than 2 μL/min. The capillary number (Ca) was in a range of $5\times10_{-5}$-$5\times10_{-3}$ and the Reynolds number (Re) was less than 0.005.

Figure 12:
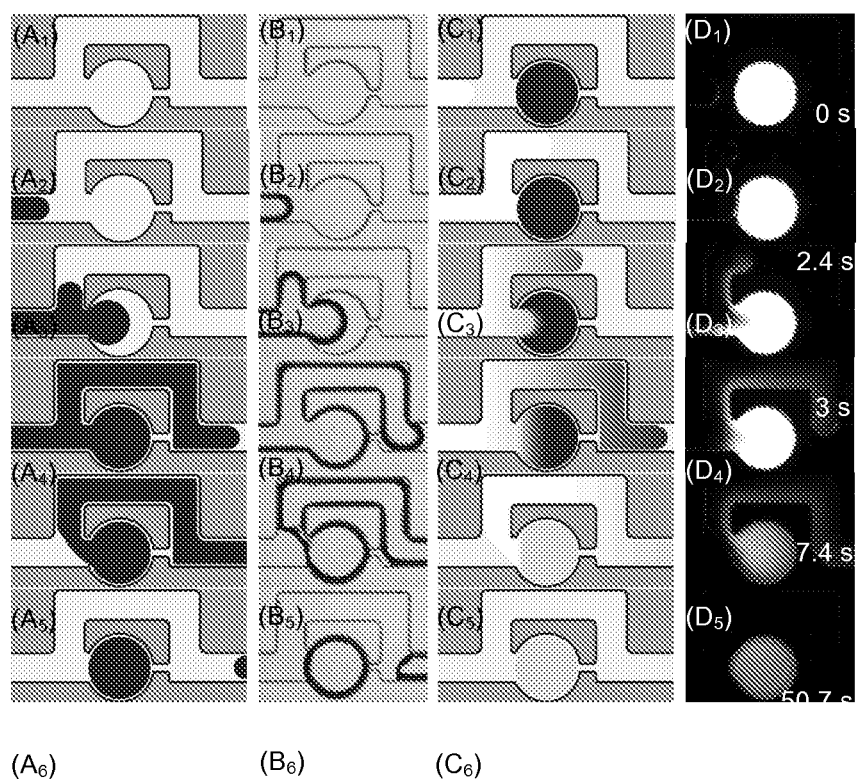
FIGS. 12 A1, B1, C1, D1, A2, B2, C2, D2, A3, B3, C3, D3, A4, B4, C4, D4, A5, B5, C5, D5, A6, B6, C6, and D6 are schematic illustrations and snapshots of the droplets trapping (A, B) and diluting (C, D) processes.
Figure 13A:
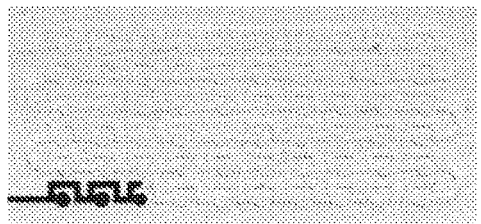
FIGS. 13A-F are images of snapshots of the droplets trapping (A-C) and diluting processes (D-F) by slugs.
Figure 13B:
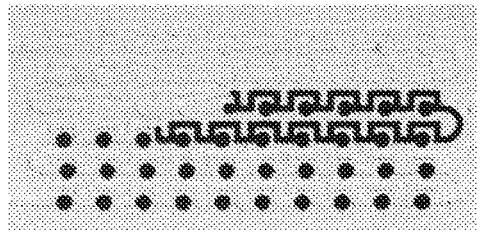
Figure 13C:
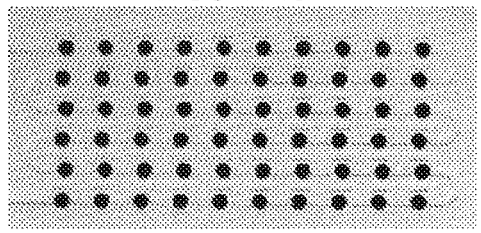
Figure 13D:
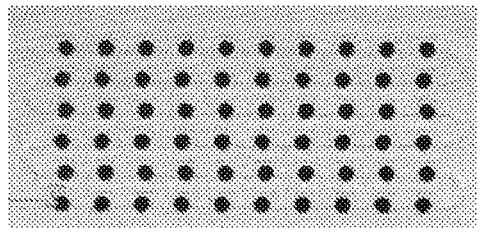
Figure 13E:
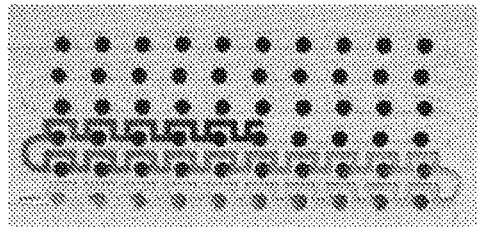
Figure 13F:
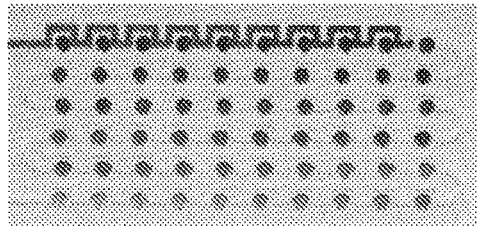

FIGS. 12 A1, B1, C1, D1, A2, B2, C2, D2, A3, B3, C3, D3, A4, B4, C4, D4, A5, B5, C5, D5, A6, B6, C6, and D6 are schematic illustrations and snapshots of the droplet trapping (A, B) and diluting (C, D) processes. FIGS. A1 and B1 show traps filled with oil. FIGS. A2 and B2 show a trapping slug approaching. FIGS. A3 and B3 show the trapping slug entering into the trap. FIGS. A4 and B4 show a trapping slug flowing. FIGS. A5 and B5 show the tail of the trapping slug pinching off. FIGS. A6 and B6 show the trapped droplet. FIGS. C1 and D1 show the diluting slug approaching. FIGS. C2 and D2 show the diluting slug contacting with the droplet. FIGS. C3 and D3 show the oil layer between the diluting slug and droplet breaking up. FIGS. C4 and D4 show diffusion. FIGS. C5 and D5 show the tail of the diluting slug pinching off. FIGS. C6 and D6 show the diluted droplet. FIGS. B1-B6 show bright field views of a 10^-3 M fluorescein droplet trapped with a continuous phase flow rate of 1 μL/min. FIGS. D1-D6 show fluorescent images of a 10^-3 M fluorescein droplet diluted by a 0.8-μL-water slug at a flow rate of 0.5 μL/min. Oil: 0.1% (w/v) Span 80 in mineral oil.

The mechanisms of the droplet trapping and diluting by slugs are illustrated in FIG. 12A, C. The chip was filled with oil first. The aqueous slug was then introduced into the trapping zone. Due to the resistance of the upper branch being 3 times lower than the lower one, the slug preferred to flow upwards and thus blocked the channel and made its resistance increase, which then induced the slug to flow into the trap in the lower branch and made the whole trap occupied, thus blocking the restriction channel. The slug, propelled by the oil continuous phase, continued to flow through the upper channel until its tail broke free of the aqueous liquid in the trap. After that, one portion of the slug was divided into one trap, and a droplet was generated.

The minimum volume of the trapping slug can be calculated by multiplying the volume of each trap with the number of traps. For this work, each trap volume was 30 nL, and 60 traps were fabricated in the chip, so a 2 µL trapping slug was aspirated into the cartridge for filling in all the traps with droplets.

For the diluting slug, it is preferable to use pure water or buffer solution, although other liquids can be used. The diluting slug was infused and induced to flow through the trapping zone at a certain flow rate. It made a contact with each of the trapped droplets, followed by the rupture of the oil film between the two aqueous liquids. Coalescence and mutual diffusion occurred afterwards. The diffusion times for all the trapped droplets were almost identical. However, the head of the slug, like a sampler, became more and more concentrated as it traveled past each droplet due to the diffusive exchange, turning itself into a slug with a concentration gradient of solute which was at least partially taken away from the droplet by the slug. The slug had the highest solute concentration at the front while the lowest concentration was at the tail. At the same time, the traveling slug continually fed fresh diluting liquid to the diffusion interface to dilute the droplet, which led to a serial dilution of the pre-trapped droplets in the array and the generation of a gradient of droplet concentrations throughout the array.

FIGS. 13A-F are images of snapshots of the droplets' trapping (A-C) and diluting processes (D-F) by slugs. Oil: 0.1% (w/v) Span 80 in mineral oil; flow rate for trapping and diluting slugs: 1 µL/min and 0.5 µL/min. We used 10^-3 M fluorescein solution as a trapping slug and water as a diluting slug to demonstrate the trapping and diluting mechanics in the first trap of the trapping zone. The bright field views and fluorescent images are shown in FIG. 12 B, D. Snapshots taken from the process of a droplet array of black dye diluting by water are shown in FIG. 13.

Figure 14A:
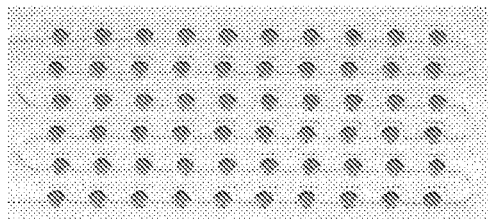
FIG. 14A is an image of blue dye trapped and FIG. 14B is an image showing dilution by a 2.2-µl water slug.
Figure 14B:
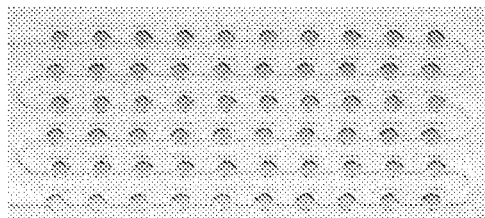
Figure 14C:
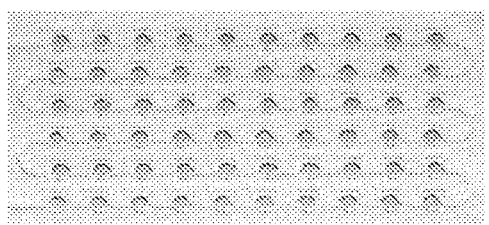
FIG. 14C is an image showing dilution by yellow dye generating concentration gradients in both blue and yellow.

FIG. 14A is an image of blue dye trapped and diluted by a 2.2-µL water slug, and FIG. 14B is a similar image with a 2.2-µL yellow dye slug. Oil: 0.1% (w/v) Span 80 in mineral oil; flow rate for trapping, diluting, and mixing slugs: 1 µl/min, 0.5 µl/min, and 0.5 µl/min respectively. After dilution, the gradient droplets could be mixed with another reagent to generate microreactors as FIG. 14A, B shown, the blue droplets with a gradient was mixed with a yellow slug to form a blue-yellow dyes mixture with different mixing ratios, where the yellow ingredient was decreasing in the droplet array.

Figure 15A:
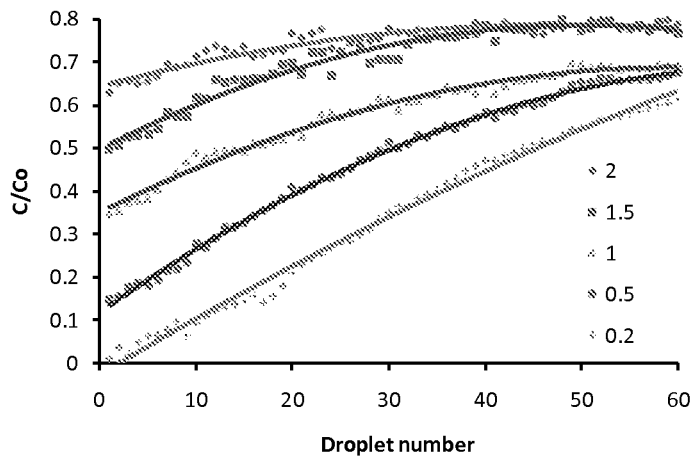
FIGS. 15A-15C show concentration profiles of the trapped droplets after diluted by (A) a 2.2 µL slug at the flow rates of 0.2 µL/min, 0.5 µL/min, 1.0 µL/min, 1.5 µL/min and 2 µL/min, respectively; (B) 0.8 µL, 1.5 µL and 2 µL slug at the flow rate of 0.5 µL/min; (C) three 1.5 µL slugs at the flow rate of 0.5 µL/min. Oil: 0.1% (w/v) Span 80 in mineral oil.
Figure 15B:
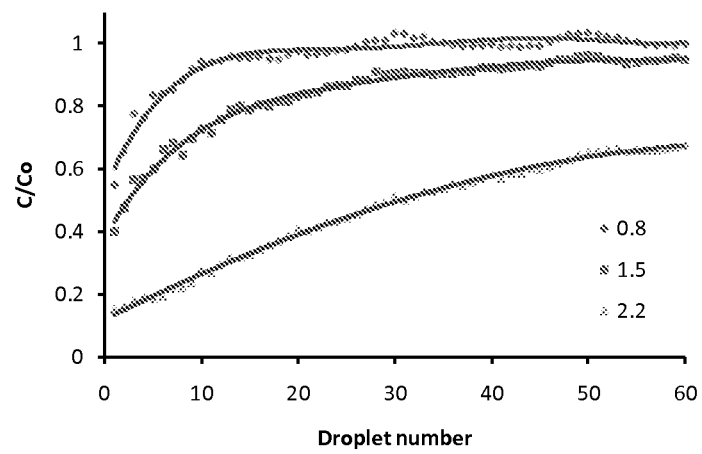

FIG. 15 shows concentration profiles of the trapped droplets after diluted by (A) a 2.2 µL slug at the flow rates of 0.2 µL/min, 0.5 µL/min, 1.0 µL/min, 1.5 µL/min and 2 µL/min, respectively; (B) 0.8 µL, 1.5 µL and 2 µL slug at the flow rate of 0.5 µL/min; (C) three 1.5 µL slugs at the flow rate of 0.5 µL/min. Oil: 0.1% (w/v) Span 80 in mineral oil.
Flow Rate.

The effect of flow rate on diluting a pre-trapped droplet array was investigated by using a same volume of 2.2 µL diluting slug. For the flow rates of 2, 1.5, 1, 0.5 and 0.2 µL/min, the times for diffusion between the traveling slug and each of the trapped droplets were 66, 88, 132, 264 and 660 s, respectively. With the diffusion time increasing, the droplet array was getting further diluted and a lower concentration gradient was produced. The result is shown in FIG. 15A.
Volume of Diluting Slug.

We varied volumes of the diluting slug as 0.8 µL, 1.5 µL and 2.2 µL to dilute a same droplet array of black dye at a fixed flow rate. During the diluting process, the dye droplets were confined inside the trap, while the fresh diluting water was continually fed to the diffusion interface by the traveling slug. The molar flux of the dye from droplet to slug is matched by the molar flux of water in the opposite direction. This means larger volume of diluting water would lead to more dye transferred into slug. Therefore, as a result shown in FIG. 4b, the droplet array was getting more diluted as the volume of diluting slug increased.
Number of Diluting Slugs.

Figure 15C:
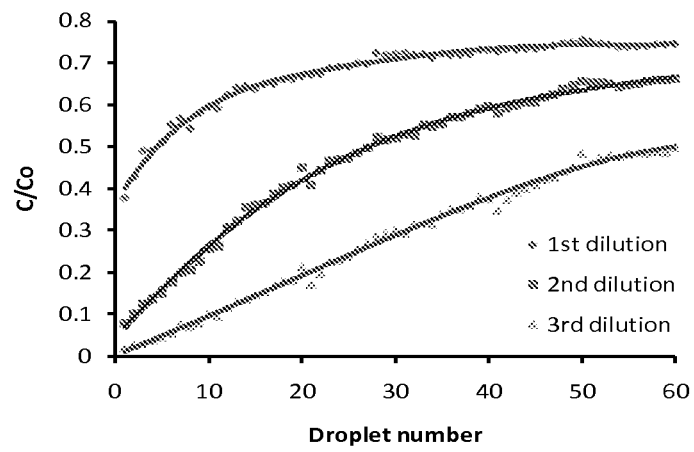

One feature of this technique is that it could perform multiple dilutions to the pre-trapped droplets by introducing several diluting slug to the array. FIG. 15C shows a droplet array of black dye diluted by three 1.5 µL water slugs at flow rate of 0.5 µL/min. After each dilution, a gradient with lower concentration span was obtained.

We also investigated the diluting efficiency of this technique by diluting a 10^-3 M fluorescein droplet with several separated water slugs. Limited by the sensitivity of the camera, we brought the concentration of the droplet down to the order of 10^-8 M after four 2.2 µL slugs diluting at flow rate of 0.5 µL/min.

Figure 16:
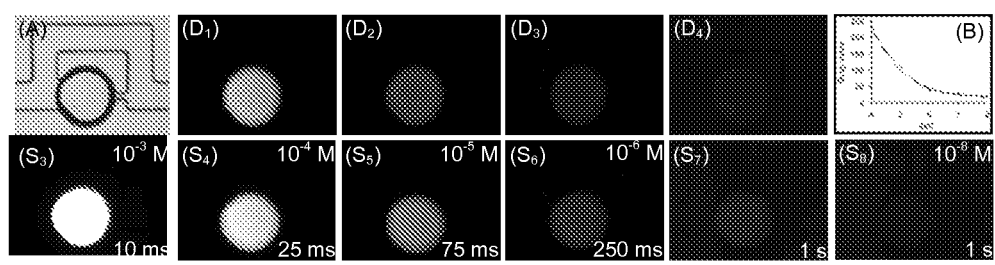
FIG. 16A is a bright field view of a trapped 1e-3 M fluorescein sodium droplet.

FIG. 16A is a bright field view of a trapped 10^-3 M fluorescein sodium droplet. (S3-S8) Fluorescent images of the standard fluorescein droplets from $10^{-3}$ M to $10^{-8}$ M, respectively. (D1-D4) Fluorescent images of the diluted fluorescein droplets after each diluting by a 2.2 µL—water slug at flow rate of 0.5 µL/min. Subscript n indicates the number of the diluting slugs. The exposure time of each fluorescent image was shown on the picture. FIG. 16B is the standard curve and the relative intensities of the diluted fluorescein droplets. Oil: 0.1% (w/v) Span 80 in mineral oil. The results are shown in FIG. 16. We believe that much lower concentrations could be achieved just by reducing the flow rate, increasing the volume or the number of the diluting slug. There is no limit in this technique to get a droplet gradient with concentration as low as one desired.

Here we report a microfluidic device that generates arrays of droplets with concentration gradients. The droplet was in nL-scale and the consumption of each sample and reagent were less than 3 µL for generating 60 droplets. Higher performance could be achieved by decreasing the trap size and increasing amount of traps. We believe smaller trap size would be benefited to promote mass transfer and induce higher dilution (mixing) efficiency. We demonstrate the capabilities of the microfluidic device using dyes and polystyrene beads as bionic cells. 5-order span of gradient was obtained, and further dilution could be achieved by adding more diluting slug, reducing diluting flow rate or increasing the volume of diluting slug. This facile feature makes it suitable for high-throughput screening, especially in preliminary screening nowadays.

Cytotoxicity testing is an important aspect of cancer drug discovery. Often a chemotherapeutic drug is tested by serial dilution in multi-well plates containing tumor cells and identifying the concentrations. Manual methods of sample preparation are laborious as the number of well plates increase and robotic methods are expensive. The high throughput nature of this method, combined with the potential for multiplexing, should allow rapid screening of libraries of cancer drug candidates on a variety of tumor cell lines.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of transporting one or more drops, cells, or compositions and forming a droplet-based concentration gradient of the one or more drops, cells, or compositions in a first solution through a microfluidic device, wherein the method comprises:

providing a sample solution comprising the one or more drops, cells, or compositions to an inlet of an microfluidic device, wherein the microfluidic device comprises the inlet in fluid communication with one or more conduits, one or more parking loops (12) connected to the one or more conduits, each parking loop (12) comprising a bypass channel (14) and a lower branch with a fluidic trap (16) capable of retaining one or more drops of the sample solution, wherein the bypass channel (14) is in fluid communication with one or more outlets, the bypass channel (14) has a smaller hydrodynamic resistance than the lower branch with the fluidic trap (16), wherein a hydrodynamic resistance ratio ($R_T/R_B$) between the lower branch with the fluidic trap (16) and the bypass channel is from 1.5 to 3.2;

filling at least one of the fluidic traps (16) with the sample solution by hydrodynamic self-rectification;

forming the droplet-based concentration gradient of the one or more drops, cells, or compositions in the first solution by moving the first solution through the one or more conduits such that the first solution merges with the stationary sample solution filled within the at least one of the fluidic traps (16) and thereby reducing a concentration of the sample solution within the at least one of the fluidic traps (16) and leaving a volume of the merged first solution and sample solution within the at least one of the fluidic traps (16) unchanged.

2. The method of claim 1, further comprising introducing a fluid into the inlet to dilute the sample solution thereby forming a gradient slug in the one or more conduits.

3. The method of claim 1, wherein the microfluidic device is adapted to separate blood or other cells.

4. The method of claim 1, wherein the sample solution does not include a surfactant.

5. The method of claim 1, wherein the hydrodynamic resistance ratio ($R_T/R_B$) between the lower branch and the bypass channel is from 1.0 to 2.0.

6. The method of claim 1, wherein the hydrodynamic resistance ratio (($R_T/R_B$) between the lower branch and the bypass channel is from 1.4 to 1.6.

7. The method of claim 1, wherein the first solution in the microfluidic device is at least partially aqueous.

8. The method of claim 1, wherein the microfluidic device comprises an array of parking loops.

9. The method of claim 8, wherein the array of parking loops is formed into at least one of a square array, a triangular array, a pentagonal array, a hexagonal array, a rectangular array, a polygonal array, a circular array, an oval array, an undular array, or a three-dimensional array.

10. The method of claim 8, wherein the array of parking loops is in series.

11. The method of claim 1, wherein:

the microfluidic device further comprising a reagent inlet and a mixing channel in fluid communication with a T-junction in fluid connection with the one or more outlets from the one or more bypass channels; and further comprising controlling a passage of the droplet-based concentration gradient of the one or more drops, cells, or compositions in the first solution through the mixing channel by introducing a reagent drop into the reagent inlet.

12. The method of claim 1, wherein the sample solution is at least partially aqueous.

13. The method of claim 8, further comprising the steps of:

introducing one or more reagents into the array of parking loops such that the one or more reagents are trapped in the fluidic traps; and subsequently producing a concentration gradient of the one or more reagents in a diluting plug by introducing the diluting plug into the array of parking loops and sequentially removing a portion of the one or more reagents from the fluidic traps as the diluting plug moves past the fluidic traps and through the bypass channels.

14. The method of claim 1, wherein the one or more parking loops is in fluid communication with at least one of the following additional reservoirs: mixing tubes, concentrator arrays, conduits, outlets, reagent reservoirs, valves, particle segregators, filters, plugs, or pumps.

15. The method of claim 1, wherein the fluidic trap is wider than the one or more conduits or the bypass channel.

16. The method of claim 13, further comprising fragmenting the diluting plug into a series of drops or plugs that are shorter than the diluting plug by pumping an oil into a side channel in fluid communication with a T-junction in fluid communication with the one or more outlets from the one or more bypass channels and an outlet channel.

\* \* \* \* \*